(12) United States Patent
Ruch

(10) Patent No.: US 6,375,667 B1
(45) Date of Patent: Apr. 23, 2002

(54) NASAL DILATOR

(75) Inventor: Jeffrey T. Ruch, Laguna Beach, CA (US)

(73) Assignee: North American Financial Corp, Tortola (VG)

( * ) Notice: Subject to any disclaimer, the term of this patent is extended or adjusted under 35 U.S.C. 154(b) by 0 days.

(21) Appl. No.: 09/404,214

(22) Filed: Sep. 23, 1999

(51) Int. Cl.[7] .............................................. A61M 29/00
(52) U.S. Cl. ................................ 606/199; 128/200.24
(58) Field of Search ................. 128/200.24; 606/199, 606/204.45; 602/41, 44, 47, 54, 57–59

(56) References Cited

U.S. PATENT DOCUMENTS

| | | | | |
|---|---|---|---|---|
| 5,890,486 A | * | 4/1999 | Mitra et al. | 128/200.24 |
| 5,957,126 A | * | 9/1999 | Neeser | 128/200.24 |
| 6,065,470 A | * | 5/2000 | Cromvoirt et al. | 128/200.24 |

* cited by examiner

Primary Examiner—Glenn K. Dawson
(74) Attorney, Agent, or Firm—G. Donald Weber, Jr.

(57) ABSTRACT

A nasal dilator that prevents the outer wall tissue of the nasal passages of the nose from drawing in during breathing includes a flexible strip of material having a first end region, a second end region and an intermediate segment. The dilator further includes first and second resilient bands secured to one surface of the strip the first and second end regions, and a third resilient band secured to a second surface of the flexible strip adjacent the intermediate segment. The ends of the third resilient band overlie the inward ends of the first and second resilient bands whereby the third resilient band extends over and at least partly beyond the bridge on both sides of the bridge of the nose. A first adhesive surface covers the first surface of the strip of material so that there is a perimeter of space formed around and between the first and second resilient bands which are inset centrally on the strip. Adhesive or auxiliary supports can be used to secure the ends of the third band to the second surface of the strip.

20 Claims, 2 Drawing Sheets

NASAL DILATOR

BACKGROUND OF THE INVENTION

1. Field of the Invention

This invention relates, generally, to the field of dilator devices for the nose and, in particular, to a nasal dilator to urge the nasal passages of the nose open and for preventing outer wall tissue of nasal passages of a person's nose from drawing in during breathing.

2. Prior Art

A portion of the human population has some malformation of the nasal passages which makes breathing difficult. Examples of such malformations are a deviated septum and swelling due to allergic reactions.

The lower portion of the nostril, immediately above the entrance to the nostril, is known as a vestibule. The vestibule tapers inwardly to a narrowed, neck-like area called the nasal valve. Posterior to the nasal valve, the nasal passages widen out again. Nasal obstructions commonly occur at the nasal valve in individuals who have swelling due to allergic reactions, a deviated septum or similar condition, to the point that the nasal valve may be substantially blocked. Commonly, the lateral wall (i.e., the outer wall tissue of the nasal passage) at the nasal valve is loose with the result that the outer wall tissue draws in during the process of inhalation to substantially or completely block the passage of air through the nasal passage.

Blockage of the nasal passages is obviously an inconvenience to persons who experience this difficulty. In addition, sustained mouth breathing over a long period of time may cause lung irritation due to the inhalation of foreign particles that would otherwise be filtered by breathing through the nose. Blockage of the nasal passages is particularly uncomfortable at night, since nasal blockage can lead to sleep disturbances, sleep irregularities and/or snoring. In addition, a person with such a condition may often awaken because of not easily inhaling sufficient quantities of oxygen.

The most common approach to a serious and chronic nasal blockage problem as described above is a surgical attempt to correct the malformation of the nasal passages. However, surgery is expensive and may not, ultimately, correct the problem.

Another instance wherein enhanced breathing is desirable is during strenuous physical activity including, but not limited to, sports contests. In these cases, the individual needs as much breathing ability as possible to maintain a high level of oxygen intake.

As an alternative to surgery and/or to permit enhanced breathing, nasal dilators for aiding breathing through the nose are generally known. There are several known forms of dilator used for this purpose. One such dilator is in the nature of a band or extension applied to the nose from one nasal passage, over the bridge of the nose, to the other nasal passage. This dilator is formed of a flexible material which has sandwiched with it a resilient spring material. Both the flexible material and the spring are normally planar. When the pad is placed on the nose, it sticks to the skin of the nose, and the action of the spring causes the nasal passages to be urged open.

U.S. Pat. No. 4,414,977 to Rezakhany discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the nasal valve within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are uncomfortable to wear because they must be inserted within the nasal passages and may cause irritation and itching. In addition, these nasal dilators must be custom-made to fit each nasal passage of an individual.

Another nasal dilator is disclosed in the U.S. Pat. No. 1,292,083 to Sawyer. This nasal dilator includes pads of adhesive material to which are attached metal loops. The pads are applied to the exterior surface of the nose above the nostrils. Once the pads are affixed, a dilating member is connected with each of the loops. The dilating member consists of a metal wire that provides a spring force which is directed outwardly or upwardly when hooked ends of the dilating member are engaged with the loops of the pads.

A further nasal dilator is disclosed in the U.S. Pat. No. 1,950,839 to Chirila. This nasal dilator is similar to that of Sawyer but employs suction cups to secure a dilating member to the exterior surface of the nose.

These nasal dilators are not always effective in insuring free breathing because of the multiple element configurations which are designed to be assembled and then disassembled wherein they can easily become disengaged from the elements (i.e., the pads in Sawyer and the suction cups in Chirila) that secure the dilating members to the exterior of the nose. This unwanted disengagement of the elements could result in injury to the wearer of the nasal dilators.

A still further nasal dilator is disclosed in the International Application Published Under The Patent Cooperation Treaty WO 92/22340 to Johnson. This nasal dilator comprises a truss member that includes a flexible strip of material having a first end region, a second end region and an intermediate segment. The first and second end regions are adapted to engage the outer wall tissue of first and second nasal passages of the nose and are secured thereto via an adhesive substance. The truss member further includes resilient bands that are secured to the strip of material by way of strips of double-sided adhesive foam tape. The resiliency of the bands acts to stabilize the outer wall tissue and thereby prevents the outer wall tissue of the nasal passages from drawing in during breathing.

The curved ends of the strip of material extend past angled ends of the resilient bands. However, the nasal passages are not urged open as much or as little as they could usefully and safely be opened. Also, this device consists. of multiple components forming the pad in a sandwich relationship which arrangement is unduly complicated.

Other Patents of Interest

U.S. Pat. No. 5,546,929, NASAL DILATOR, J. D. Muchin.

U.S. Pat. No. 5,533,499, NASAL DILATOR, B. C. Johnson.

U.S. Pat. No. 5,533,503, NASAL DILATOR, W. J. Doubek et al.

Other Publications

Petruson, Bjorn, "Snoring Can Be Reduced When the Nasal Airflow is Increased by the Nasal Dilator Nozovent", *Arch. Otolaryngol Head Neck Surg.* (1990) vol. 116, pp. 462–464.

Petruson, Bjorn; "Improvement of the Nasal Airflow by the Nasal Dilator Nozovent", *Rhinology,* vol, 26, pp. 289–292 (1988).

Petruson, Bjorn; "Decreased Nasal Resistance by the Nasal Dilator Nozovent® can Reduce Snoring", World Congress on Chronic Rhonchopathy (May 1989).

Petruson, Bjorn et al.; "The Importance of Nose-breathing for the Systolic Blood Pressure Rise During Exercise", *Acta Otolaryngol,* Stockholm, 109: 461–466, (1990).

E. N. T. Spring Symposium; "Report of a Symposium at the Royal Society of Medicine, London, May 21, 1991" pp. 1–4, A Simple, but Effective Way to Treat Snoring, Petruson.

Petruson, Bjorn; "Two New Ways for Nasal Administration of Drugs with the Nasal Dilator Nozovent", Abstract, ENT-Department, University of Goteborg, University of Goteborg, Sahlgrens's Hospital, 413, 45 Goteborg, Sweden.

Hoijer, Ulf, et al., "The Effects of Nasal Dilation on Snoring and Obstructive Sleep Apnea", *Arch. Otolaryngol Head Neck Surg.* (1992) vol. 118, pp. 281–284.

Lancer, J. M., et al., "The Francis Alae Nasi Prop and Nasal Airway Resistance to Airflow," *The Jounal of Laryngology and Otology* (1986) vol. 100, pp. 539–541.

Ford, Charles, et al., "A Nasal Prothesis for Treatment of Nasal Airway Obstruction, " *Rhinology* (1985) vol. 23, pp. 223–229.

SUMMARY OF THE INVENTION

The present invention is an improved nasal dilator for preventing outer wall tissue of nasal passages of a nose from drawing in during breathing. The nasal dilator comprises a flexible support member comprising a thin, flat strip of material having a first end region adapted to engage the outer wall tissue of a first nasal passage, and a second end region to engage the outer wall tissue of a second nasal passage. The first and second end regions of the support member are coupled to one another by an intermediate segment. The intermediate segment is configured to traverse a portion of the nose located between the first and second nasal passages. A pair of resilient bands are mounted on and extend axially along one surface of the support member and have end portions that terminate in the first and second end regions. A third resilient band is mounted on the opposite surface of the support member at the intermediate segment with the ends thereof overlapping the adjacent ends of the first and second resilient bands. The first and second resilient bands, when the dilator is in place, act to stabilize, and thereby prevent, the outer wall tissue of the first and second nasal passages from drawing in during breathing.

The first and second resilient bands are oriented in line with one another and substantially along the longitudinal axis of the flexible strip. The resiliency of the first and second resilient bands prevents the outer wall tissue of the first and second nasal passages from drawing in during breathing.

An adhesive substance on the first surface of the flexible strip of material acts to releasably secure the dilator to the outer wall tissue of the first and second nasal passages. The adhesive is between the first and second bands and the strip. A surface perimeter area is formed between the outer edge of the strip and the peripheral edge of the bands. Thus, the surface perimeter area includes an adhesive for adhering to skin of the nose.

A release liner covers the adhesive substance on the first surface of the flexible strip and is readily removable from the strip to expose the adhesive substance and permit the dilator to be secured to the outer wall tissue of the first and second nasal passages.

This nasal dilator is an efficient design that can be efficiently manufactured. Typically, the strip is made of a breathable material. Thus, the nasal dilator can be comfortably worn for extended therapeutic periods.

The invention is further described with reference to the accompanying drawings.

DESCRIPTION OF A PREFERRED EMBODIMENT

FIGS. 1–4 are referred to concurrently.

Figure 1:
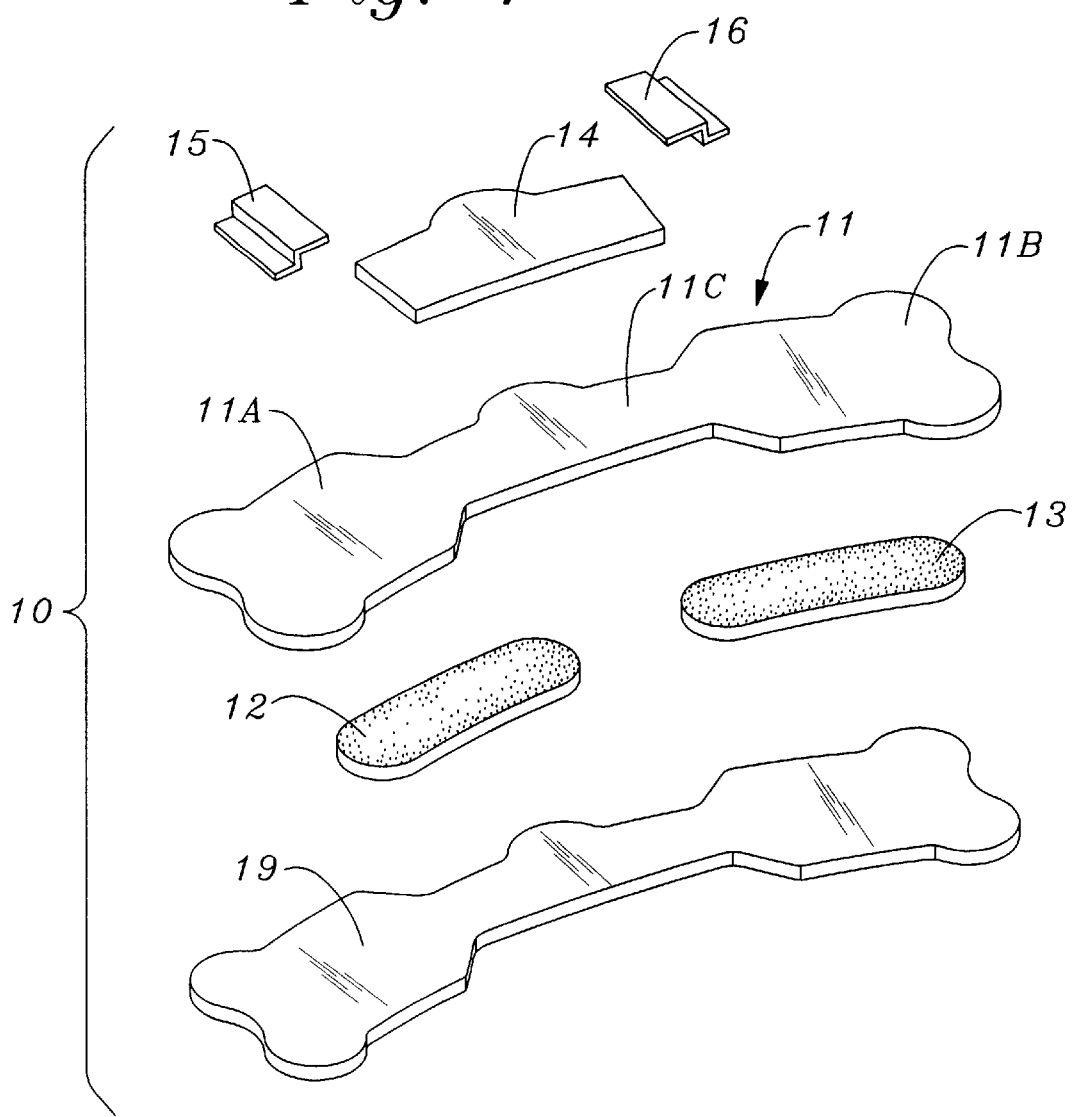
FIG. 1 is an exploded perspective view showing the components of the nasal dilator in accordance with the present invention.
Figure 2:
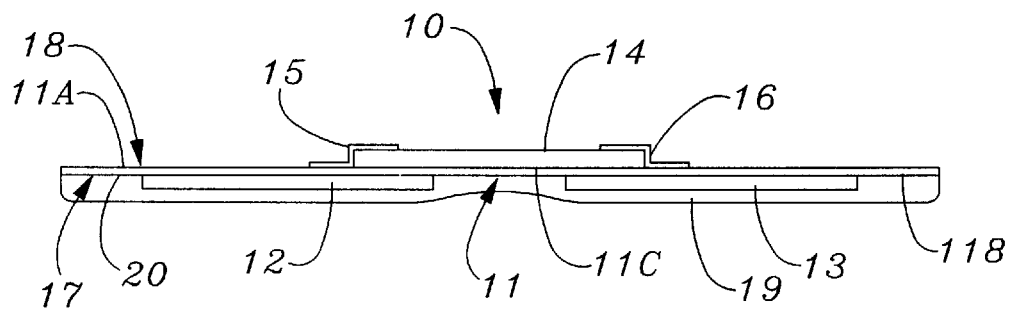
FIG. 2 is a side view of the dilator.
Figure 3:
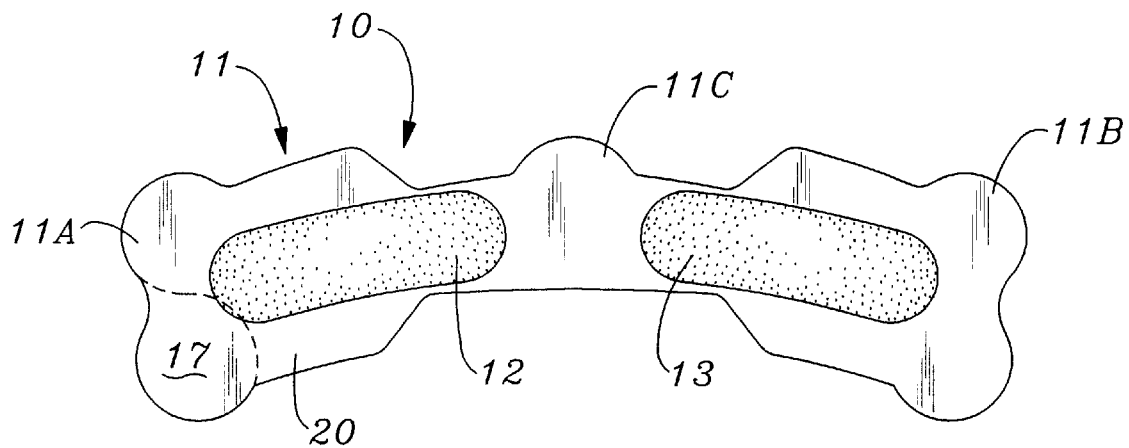
FIG. 3 is a bottom view of the dilator with the release liner removed.
Figure 4:
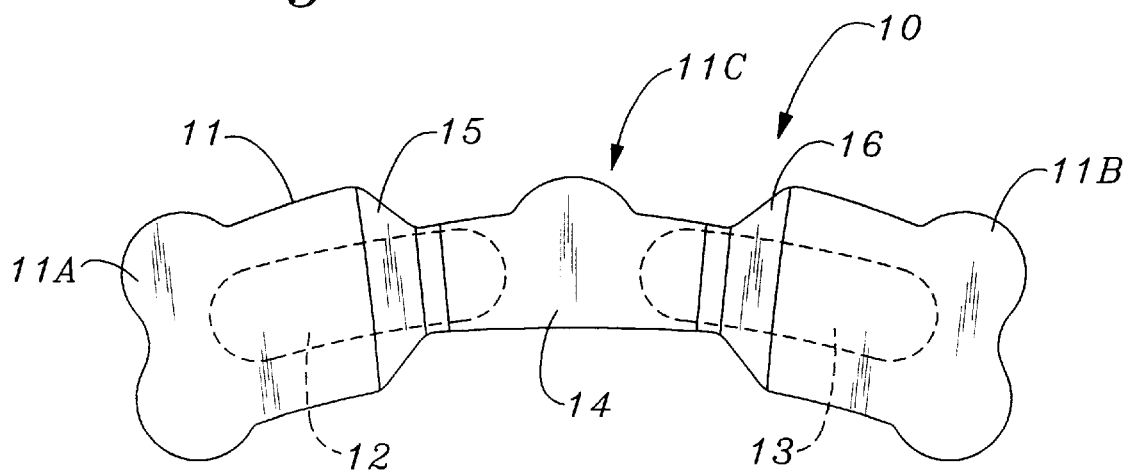
FIG. 4 is a top view of the dilator.

A side view of nasal dilator 10 in accordance with the present invention is illustrated generally in FIG. 2. The dilator 10 includes an elongated support member 11 for bridging the human nose. The support member 11 is formed of a synthetic resinous material such as, but not limited to, a polyethylene strip. In a preferred embodiment, the strip is 4 mil thick. The support member 11 has an arcuate outer configuration and opposite flat surfaces 17 and 18. The lower surface 17 extends over and may adhere to the bridge of the nose.

A medical grade acrylic adhesive layer 20, having a thickness of about 2 to 2.5 mils, is provided on the surface 17. The strip 11 is clear, durable, and has dimensional stability but is capable of stretching to conform to the individual nose. It is resistant to mild acids, alkalies, and salt. Further, the film strip 11 is fungus, water and corrosion-resistant. The strip may be formed of a slightly stretchable material which, in some embodiments, may be perforated.

Typically, the ends 11A and 11B are somewhat larger than the intermediate bridge 11C in order to provide suitable adhesion to the nose.

The resilient bands 12 and 13 are, generally, oval shaped pieces of a suitable material such as polyester with a medical grade adhesive on the outer surface thereof. The bands 12 and 13, for example, of about 7 mil thickness, are adhered to the under surface 17 of the strip 11 with the adhesive layer of the bands facing outwardly. Thus, the bands 12 and 13 will also adhere to the nose.

The bands 12 and 13 are disposed, generally, on the center line of the strip 11 in an in-line relationship. The exterior ends of the bands 12 and 13, respectively, terminate within the end regions 11A and 11B, respectively, of the strip member 11. The interior ends of the bands 12 and 13 are disposed within the intermediate bridge 11C but are spaced apart from each other.

A conventional release liner 19, formed of polycoated Kraft paper, for example, is removably attached to the adhesive layer on the surfaces of bands 12 and 13 as well as the lower surface 17 of strip 11.

A third flexible, resilient band 14 is also generally oval shaped to conform to the configuration of the intermediate bridge 11C. The band 14 is, typically, formed of a polyester with an acrylic adhesive thereon to adhere to the strip 11. The band 14 is, in a preferred embodiment, approximately 10 mil thick, although variations in this dimension are anticipated. The band 14, as noted, substantially covers the entire intermediate bridge 11C of the strip 11. As a consequence, the ends of the band 14 overlie the interior ends of the bands 12 and 13 on the lower surface 17 of the strip 11. This arrangement permits the bands 12, 13 and 14 to be relatively short but to collectively influence the operation of the dilator 10 when placed on a nose.

Also, by substantially conforming to the intermediate bridge 11C of the strip 11, the band 14 imparts additional strength to the dilator 10 at the narrow part thereof.

In one embodiment, the clamps 15 and 16 are attached to the ends of band 14 and to the upper surface 18 of strip 11. The clamps, typically, polyethylene with an acrylic adhesive surface, are approximately 3 mil thick and extend across the entire width of the band 14 on the strip 11 at the juncture point. The clamps 15 and 16 assist in preventing the band 14 from separating from the strip 11 under stressed conditions when the dilator is in use.

Using the Dilator

When the dilator 10 is located over the bridge of the nose of the user, the flat surface 18 of the ends 11A and 11B of the support member 11 extend over both sides of the bridge of the nose.

When the dilator 10 is located on the nose of a wearer, the ends 11A and 11B of the support member 11 are urged outwardly by the interaction of bands 12, 13 and 14, to thereby separate the nasal passages of the wearer. When in position on the nose, flat surface 17 of the dilator 11 engages directly on the nose through the adhesive layer 20 on the surface 17 after the liner 19 has been removed.

Thus, there is shown and described a unique design and concept of a nasal dilator. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

What is claimed is:

1. A nasal dilator that prevents the outer wall tissue of the nasal passages of the nose from drawing in during breathing including,
   a strip of flexible material having a first end region, a second end region and an intermediate segment,
   first and second resilient bands secured to a first surface of said strip adjacent said first and second end regions thereof,
   a third resilient band secured to a second surface of said strip at said intermediate segment, and
   a first adhesive surface covering said first surface of said strip of flexible material so that there is a perimeter of space formed around and between said first and second resilient bands which first adhesive surface is used to adhere the dilator to the nose of the user of the dilator.

2. The dilator recited in claim 1 wherein,
   the ends of said third resilient band overlie the adjacent ends of said first and second resilient bands whereby the third resilient band is adapted to extend over and at least partly beyond both sides of the bridge of the nose of the user of the dilator.

3. The dilator recited in claim 1 including,
   a second adhesive surface disposed between said third band and the second surface of said strip to connect said third band with said strip.

4. The dilator recited in claim 1 including,
   auxiliary supports to secure the ends of said third band to said second surface of said strip.

5. The dilator recited in claim 1 including,
   a release liner removably attached to said first adhesive surface of said strip.

6. The dilator recited in claim 5 wherein,
   said release liner removeably covers said first and second bands prior to application of the dilator to the nose.

7. The dilator recited in claim 1 wherein,
   said first and second end regions are adapted to engage the outer wall tissue of first and second nasal passages of the nose of the user and said intermediate segment is configured to traverse a portion of the nose located between the first and second nasal passages.

8. The dilator recited in claim 1 wherein,
   said first and second bands are axially aligned on said strip.

9. The dilator recited in claim 1 wherein,
   the resiliency of said first and second resilient bands acts to stabilize the outer wall tissue of the nose and thereby prevents the outer wall tissue of the first and second nasal passages from drawing in during breathing.

10. The dilator recited in claim 1 wherein,
    said strip of flexible material is perforated.

11. A nasal dilator that prevents the outer wall tissue of the nasal passages of the nose from drawing in during breathing including,
    a strip of flexible material having a first end region, a second end region and an intermediate segment,
    first and second resilient bands secured to a first surface of said strip adjacent said first and second end regions thereof with a space between the adjacent ends of said first and second bands,
    a third resilient band secured to a second surface of said strip at said intermediate segment, and
    auxiliary supports to secure the ends of said third band to said second surface of said strip.

12. The dilator recited in claim 11 wherein,
    said third resilient band includes opposite ends thereof which overlie the adjacent ends of said first and second resilient bands and the space therebetween whereby said third resilient band is adapted to extend over both sides of the bridge of the nose of the user of the dilator.

13. The dilator recited in claim 11 including,
    a first adhesive surface which covers said first surface of said strip of flexible material so that there is a perimeter of space formed around and between the first and second resilient bands which first adhesive surface is used to adhere the dilator to the nose of the user.

14. The dilator recited in claim 13 including,
    an adhesive layer disposed between said resilient third band and said strip of flexible material to connect the entire third resilient band with said strip of flexible material.

15. The dilator recited in claim 13 including,
a release liner removably attached to said first adhesive surface of said strip.

16. The dilator recited in claim 15 wherein,
said release liner removeably covers said first and second bands prior to application of the dilator to the nose.

17. The dilator recited in claim 11 wherein,
said first and second end regions are adapted to engage the outer wall tissue of first and second nasal passages of the nose of the user and said intermediate segment is configured to traverse a portion of the nose of the user which can be located between the first and second nasal passages.

18. The dilator recited in claim 11 wherein,
said first and second bands are axially aligned on said strip.

19. The dilator recited in claim 11 wherein,
the resiliency of said first and second resilient bands acts to stabilize the outer wall tissue of the nose and thereby prevents the outer wall tissue of the first and second nasal passages from drawing in during breathing.

20. The dilator recited in claim 11 wherein,
said strip of flexible material is perforated.

* * * * *